(12) United States Patent
Roback et al.

(10) Patent No.: US 7,425,309 B2
(45) Date of Patent: *Sep. 16, 2008

(54) IMMUNOLOGICAL ASSAY SYSTEM AND METHOD

(75) Inventors: John D. Roback, Decatur, GA (US); Christopher D. Hillyer, Dunwoody, GA (US)

(73) Assignee: Emory University, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/602,981

(22) Filed: Jun. 24, 2003

(65) Prior Publication Data

US 2003/0235866 A1    Dec. 25, 2003

Related U.S. Application Data

(63) Continuation-in-part of application No. 09/773,826, filed on Jan. 31, 2001, now Pat. No. 7,189,357.

(60) Provisional application No. 60/179,248, filed on Jan. 31, 2000.

(51) Int. Cl.
*G01N 33/00* (2006.01)
(52) U.S. Cl. .............................. 422/73; 422/62; 422/63; 422/68.1
(58) Field of Classification Search ................... 422/62, 422/68.1, 100, 101, 255, 63, 73
See application file for complete search history.

(56) References Cited

U.S. PATENT DOCUMENTS

| | | | |
|---|---|---|---|
| 5,273,718 A | 12/1993 | Skold et al. ................ 422/101 |
| 5,308,990 A * | 5/1994 | Takahashi et al. ........ 250/459.1 |
| 5,603,899 A | 2/1997 | Franciskovich et al. ..... 422/100 |
| 5,620,898 A | 4/1997 | Yaremko et al. ............. 436/45 |
| 5,762,878 A | 6/1998 | Clark et al. ................. 422/102 |
| 5,776,711 A | 7/1998 | Vyas et al. ................. 435/7.25 |
| 5,968,731 A | 10/1999 | Layne et al. .................... 435/5 |
| 6,008,040 A | 12/1999 | Datar ........................ 435/325 |

(Continued)

OTHER PUBLICATIONS

Supplementary European Search Report, mailed Jun. 7, 2006 in European Patent Application No. 04756077.6-2402, based on PCT/US2004/020380, filed Jun. 24, 2006, which claims priority to instant U.S. Appl. No. 10/602,981.

(Continued)

*Primary Examiner*—Jill Warden
*Assistant Examiner*—Dwayne K Handy
(74) *Attorney, Agent, or Firm*—Thomas, Kayden, Horstemeyer & Risley, LLP

(57) ABSTRACT

An immunological or immunohematological assay system is disclosed that includes a vessel capable of containing an assay sample, an incubator, a sample separation system, an image acquisition system, and a pipettor. The immunological assay system may also include a washer. Also disclosed is an immunological assay method that includes the steps of placing a immunological assay sample in a vessel, which may include a filter; adding testing reagents to the vessel; incubating the sample and reagent mixture in the vessel; separating the sample and reagent mixture in the vessel into components that have and have not reacted; and analyzing the vessel to determine the presence of interactions between the sample and reagents. The bottom of the vessel is preferably of a material that aids in spreading out the reacted components of the sample evenly over the bottom of the vessel so that interactions can more easily be analyzed.

36 Claims, 3 Drawing Sheets

U.S. PATENT DOCUMENTS 6,692,702 B1 * 2/2004 Burshteyn et al. ........... 422/101
2001/0046452 A1 11/2001 Roback et al.

OTHER PUBLICATIONS

Roback, John D. et al, "Improved Method for Fluorescence Cytometric Immunohematology Testing", Transfusion vol. 44, No. 2, Feb. 2004, pp. 187-196.

Roback, John D. et al. "An Automatable Format for Accurate Immunohematology Testing by Flow Cytometry", Transfusion, vol. 43, No. 7, Jul. 2003, pp. 918-927.

International Search Report for PCT/US04/20380, mailed Mar. 3, 2005.

* cited by examiner

IMMUNOLOGICAL ASSAY SYSTEM AND METHOD

CLAIM OF PRIORITY

This application claims priority to U.S. provisional patent application entitled "Method for Diagnostic Laboratory Testing using DFS Columns" filed on Jan. 31, 2000 and accorded Ser. No. 60/179,248, and is a continuation-in-part of and claims priority to copending U.S. utility patent application entitled, "Immunological Assay System and Method" filed on Jan. 31, 2001 now U.S. Pat. No. 7,189,357 and accorded Ser. No. 09/773,826, both of which are entirely incorporated herein by reference.

STATEMENT REGARDING FEDERALLY SPONSORED RESEARCH OR DEVELOPMENT

The U.S. government has a paid-up license in this invention and the right in limited circumstances to require the patent owner to license others on reasonable terms as provided for by the terms of Grant No.: HL66751 awarded by the National Institute of Health.

TECHNICAL FIELD

The present invention is generally related to an immunological assay system and, more particularly, is related to a system and method for separating and analyzing components of immunological and immunohematological samples.

BACKGROUND

Immunological assays are designed to detect reactions between antibodies and antigens. These assays commonly employ cells, such as red blood cells (RBCs) or beads as "antigen carriers." In the appropriate assay configuration, antibodies can cross-link the antigen carriers, generating a large three-dimensional antigen-antibody aggregate from what were initially individual antigen carriers and antibodies. In other configurations, antibodies bind to the antigen carriers without cross-linking them.

Immunohematology testing in the blood bank setting uses RBCs and antibodies to determine compatibility between transfusion donor and recipient prior to transfusion. For example, the donor and recipient are incompatible if antibodies from the recipient cross-link (agglutinate) RBCs from the donor, resulting in the formation of large RBC aggregates. Current commercially available testing reagents are designed to distinguish these aggregates from individual, non-agglutinated RBCs. For example, in standard "tube testing," RBCs are mixed with antibodies, centrifuged at approximately 1000× acceleration of gravity (g) for a brief period, approximately 30 seconds, to enhance the formation of antigen-antibody complexes, and then gently resuspended by hand in order to be able to distinguish agglutinated from non-agglutinated RBCs. Tube testing is labor-intensive, not amenable to automation, and the results are difficult to standardize from lab to lab since they depend on the skill of the individual operator.

An alternative approach used to identify agglutinated RBCs is spin column technology, which is based on standard chromatographic principles. With this methodology, tubes filled with a homogeneous matrix material, e.g., beads, gel, or polyacrylamide, are used to separate aggregated from individual RBCs. The matrix material is designed with holes or pores of a specified size such that under carefully controlled centrifugal forces large ("4+") aggregates barely enter the matrix. However, successively smaller aggregates ("3+" through "1+") do enter the matrix to increasing degrees, and non-agglutinated RBCs not only enter the matrix, but sediment completely to the bottom of the tube. In order for a single homogeneous chromatographic matrix to effectively separate individual RBCs from RBC aggregates of various sizes, a relatively long centrifugation run, approximately 10 minutes, must be carried out under carefully controlled low-speed centrifugation conditions of 80×g. Deviations from optimal centrifugation conditions, e.g., higher centrifugation speeds in an attempt to shorten the assay run, lead to poor separation of RBCs, compromising the assay ability to determine compatibility between blood donor and recipient. This methodology is to some extent amenable to automation, and less dependent on operator skill.

Spin column technology is significantly more expensive than tube testing, due to costs of producing the columns. The matrix material is in solution, and carefully controlled packaging, shipping, and storage conditions are typically necessary. In addition, testing is slower than with tube testing because of the prolonged centrifugation step, approximately 10 minutes, versus approximately 30 seconds with tube testing. Interpretation of assay results also requires operator training, since the readout is on an "analog" scale, i.e., the distance of RBC migration through the matrix must typically be estimated.

There are three main applications of this technology to immunohematology testing: forward-blood typing, reverse-blood typing, and antibody screening. Each of these will be discussed separately.

ABO/D Forward Typing

Forward typing is used to determine the presence of specific clinically-important antigens on the RBC surface. These include, but are not limited to, A-antigen, B-antigen, Rh(D)-antigen, and other RBC antigens including Kell, Duffy, etc. Usually, each of these antigens is tested for in an individual test/reaction. Thus, three separate reactions are required to identify these three RBC antigens. This protocol has conventionally required that three separate tubes/reactions be set up to detect the presence of A, B, and Rh(D) antigens on RBCs.

For A and B antigen typing, we currently use a primary mouse antibody directed against the appropriate antigen, although human antisera can also be used. In theory, these antibodies can be directly labeled with a fluorescent dye, such as fluorescein or any of a number of other commercially available dyes, provided that the analysis device, i.e., flow cytometer or other appropriate instrument, can detect them. Because A and B antigens are composed in part of sugar residues, however, most antibodies that have been prepared against these antigens are of the immunoglobulin M (IgM) class and are difficult to directly label.

IgM anti-A and anti-B antibodies have a propensity to agglutinate RBCs, which is the basis for most commercially available technologies to perform blood typing. However, RBC agglutination prevents the cells from being analyzed by flow cytometry, since the large agglutinates cannot pass through the flow cell but rather clog the flow cell requiring subsequent equipment maintenance. Thus, RBC agglutination has traditionally not been compatible with flow cytometry. Indeed, prior publications in the field have suggested that agglutination of RBCs by antibodies in fact limits the application of flow cytometry to immunohematology. Furthermore, practitioners in flow cytometry usually seek to remove aggregates/agglutinates from the samples prior to flow cytometry so as not to clog the device (e.g., Berneman, Z. N., D. R. van Bockstaele, W. M. Uyttenbroeck, C. Van Zaelen, J. Cole-Dergent, L. Muylle, and M. E. Peetermans, "Flow-Cytometric Analysis of Erythrocytic Blood Group A Antigen Density Profile," *Vox Sang* 61:265 (1991); Garratty, G., and P. A. Arndt, "Applications of Flow Cytofluorometry to Red Blood Cell Immunology," *Cytometry* 38:259 (1999); Sharon, R., and E. Fibach, "Quantitative Flow Cytometric Analysis of ABO Red Cell Antigens," *Cytometry* 12:545 (1991).

ABO Reverse Typing

Reverse typing is used to determine the presence of naturally occurring anti-A and anti-B antibodies in plasma or serum. This test serves as confirmation of the forward typing tests described above to assure that the correct blood type is assigned to an individual. Usually, each of these two antibodies is tested for in individual tests/reactions. Typically, three separate tubes are used that contain group A, B, or O reagent cells. For each tube, an individual's plasma is added, incubated, washed, and then a commercially available fluorescently labeled secondary antibody directed against human IgM is added.

As with forward typing, the presence of IgM anti-A and anti-B antibodies (in this case of human origin) has a propensity to agglutinate RBCs, which is the basis for most commercially available technologies to perform blood typing. Furthermore, as above, RBC agglutination prevents the cells from being analyzed by flow cytometry, since the large agglutinates cannot pass through the flow cell but rather clog the flow cell requiring subsequent equipment maintenance.

Screening for Unexpected RBC Alloantibodies

In individuals, patients, or blood donors that have either been previously transfused or are pregnant, antibodies may have been produced against foreign RBCs (RBC alloantibodies). The same problems apply as for the forward-typing and back-typing assays, including RBC agglutination when strong alloantibodies are present.

Thus, a heretofore unaddressed need exists in the industry to address the aforementioned deficiencies and inadequacies.

SUMMARY OF THE INVENTION

Disclosed herein are systems and methods for immunological and immunohematological assaying. Briefly described, a representative assay system includes a vessel capable of containing an assay sample and a reagent, wherein the vessel comprises a bottom with an irregular or unevenly-shaped surface; a sample separation system in close proximity to the incubator; an image acquisition system in close proximity to the sample separation system; and a robotic pipettor including a robotic arm within reaching distance of the filter vessel, the incubator, the sample separation system and the image acquisition system. The vessel with an irregular or uneven surface may be a filter vessel with a filter material selected from at least one of the following: a polypropylene, a nylon, a cellulose nitrate, and polyvinylidene fluoride. Further, the filter vessel may also include a plurality of pores.

Further, disclosed are methods for immunological and immunohematological assaying. The immunological method identifies interactions between a sample and a testing reagent where one contains an antigen carrier (RBC or bead) and the other contains an antibody. In this regard, a representative method can be broadly summarized by the following: providing a vessel; reacting an immunological sample and reagent mixture in a vessel; centrifuging the sample and reagent mixture in the vessel at low speed, or for a shortened period of time; optionally washing the RBCs or other antigen carriers; and analyzing the components in the vessel to determine the presence of interactions between the sample and reagent components.

Also disclosed are immunological assay methods that include mixing a diluted immunohematological sample with a diluted reagent to form a sample mixture, analyzing the sample mixture via flow cytometry, and determining whether a predetermined component is present in the immunohematological sample. Also disclosed are immunological assay systems that include a reaction vessel, a dilute concentration of an immunohematological sample, a dilute concentration of a reagent, and a flow or capillary cytometer.

Other methods, features, and advantages of the disclosed assay systems and methods will be or become apparent to one with skill in the art upon examination of the following drawings and detailed description. It is intended that all such additional methods, features, and advantages be included within the scope of the present disclosure, and be protected by the accompanying claims.

BRIEF DESCRIPTION OF THE DRAWINGS

The disclosed assay systems and methods can be better understood with reference to the following drawings. The components in the drawings are not necessarily to scale, emphasis instead being placed upon clearly illustrating the principles disclosed herein. Moreover, in the drawings, like reference numerals designate corresponding parts throughout the several views.

DETAILED DESCRIPTION

Figure 1:
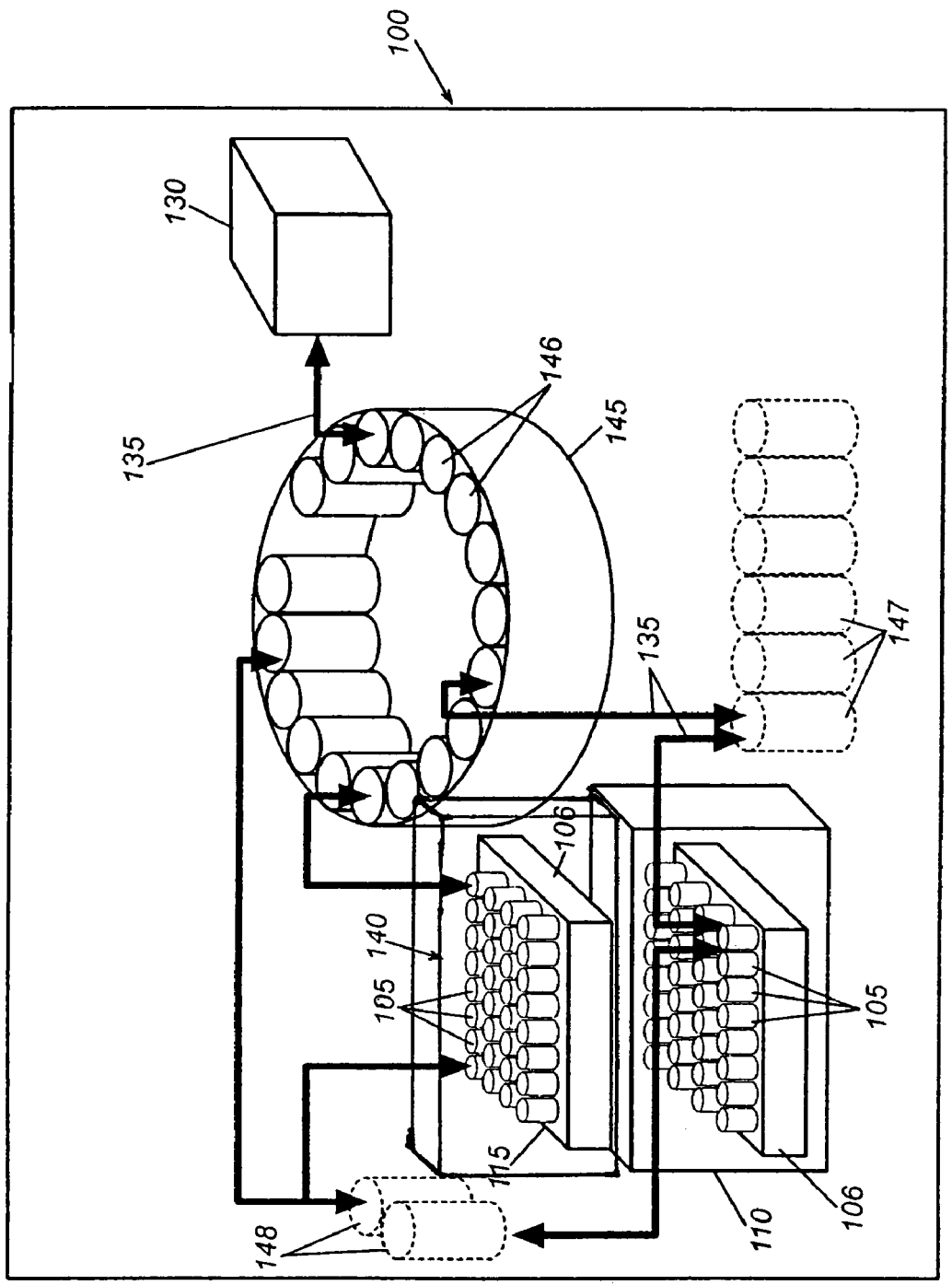
FIG. 1 is a diagram illustrating a representative disclosed immunological system.

In general, disclosed are systems and methods for separating and analyzing components of immunological and immunohematological samples. In this regard, embodiments of the immunological assay system overcome the drawbacks of current tube testing and spin column technology, while simultaneously rendering the technology of immunological assay more amenable to automation.

In one embodiment, the immunological assay system is an instrument that includes a filter vessel system having one or more filters that have discrete molecular weight and size cutoffs due to the presence of a plurality of holes or pores of specified sizes in the filter. An immunological sample is mixed with a reagent and placed above the filter(s). After vacuum, centrifugation or some other method of inducing the sample through the filter is applied, the components of the sample are separated from one another according to their size by the various filters.

In an alternative embodiment, the immunological assay system includes a reaction vessel, a dilute concentration of an immunohematological sample, a dilute concentration of a reagent, and a flow or capillary cytometer. The disclosed alternative system may also include an optional a vacuum filtration system and/or and optional centrifugation system.

In a further alternative embodiment, the immunological assay system is an instrument that includes a vessel having one or more vessels, each of which has a bottom surface with an uneven topography. "Topography" for the purposes of this document means that the bottom surface of the vessel has relief features, or surface contours such that portions of the bottom surface are raised higher than other portions, or include bumps. "Uneven" means that the bottom surface is not completely smooth, but does not mean that the raised relief on the bottom of the vessel may not be in an ordered configuration, such as rows of bumps that are evenly spaced. An inexpensive example, commercially available from numerous manufacturers, is a 96-well plate with filter material covering the bottom. Such filter plates are usually used to separate material larger than the pore size of the filter from material smaller than the pore size, for example through the application of vacuum or centrifugation to force the smaller material through the filter. In one embodiment, however, no material is required to move through the filter. In this embodiment, an immunological sample is mixed with a reagent and placed in the vessel and reacted. The filter provides an irregular surface, which retards the motion of the antigen carriers (e.g., beads or red blood cells (RBCs)) to the edge of the vessel under the influence of centrifugation, thus resulting in the antigen carriers being essentially evenly dispersed over the bottom filter material at the conclusion of centrifugation. The use of these filter plates has the benefit that the evenly dispersed film of antigen carriers do not form large agglutinates or aggregates in the presence of agglutinating antibodies, thus improving subsequent analysis of reagent interactions.

The antigen carrier herein may be, for example, synthetic beads or reagent cells, e.g., RBCs, WBCs, or platelets. For the purposes of this document and for examples, the antigen carriers will usually be referred to as RBCs, but one skilled in the art can envision other antigen carriers that may be used in the assay system and method.

As noted above, a 96-well assay plate with filter material at the bottom may be used as the vessel, numerous examples of which are commercially available. When antibodies and RBCs are reacted in the well, and then centrifuged, the irregular topography of the well bottom impedes RBC rolling and movement, causing the RBCs to spread evenly over the bottom. In contrast, if the vessel has a smooth bottom, such as a standard 96-well plastic assay plate without filter material at the bottom, the force of centrifugation may cause all of the RBCs to roll along the smooth bottom and localize into a corner of the vessel. In the presence of antibodies that bind RBCs, the tightly packed RBCs in a smooth-bottomed plate can form large agglutinates or aggregates, while in plates with irregular bottom topography the dispersed RBCs either remain as single cells or form only very small agglutinates. When the samples are analyzed using a flow cytometer as the image acquisition system, the individual cells and small agglutinates formed in plates with irregular bottom topography can be readily and accurately analyzed. In contrast, large aggregates from smooth-bottomed plates may clog and disable the cytometer, preventing or impeding sample analysis.

The disclosed immunological system can be used to measure interactions between antibodies and cells, or in some cases between antibodies and synthetic beads that can be modified and/or configured to act as antigen carriers. The immunological system can be used in at least two different ways. In one method, "cellular components" of patient samples, e.g., RBCs, white blood cells (WBCs), or platelets, are mixed with "reagent antibodies." The components of the mixture may be separated or left in situ, and then analyzed to determine the presence of interaction between the cellular components and the reagent antibodies.

In another method, the immunological system may be used in an assay method that mixes patient antibody-containing samples, e.g., plasma or serum samples, with antigen carriers that may be synthetic beads or reagent cells, e.g., RBCs, WBCs, or platelets. This mixture may be separated or left in situ, and the components are then analyzed to determine the presence of interactions between the antibody samples and the reagent cells or synthetic beads.

FIG. 1 depicts an embodiment of the immunological system 100. The immunological system 100 as shown in FIG. 1 is an instrument that includes a vessel 105 capable of containing an assay sample; an optional incubator 110 into which the vessel may be placed; a sample separation system 115 disposed in close proximity to the incubator 110 or disposed therein; an optional image acquisition system 130 in close proximity to the sample separation system 115; and an optional robotic pipettor 135 that includes a robotic arm within reaching distance to the filter vessel 105; the incubator 110; the sample separation system 115; and/or the image acquisition system 130. The immunological system 100 may also include an optional washer 140 disposed therein, and an optional turntable system 145 which has disposed therein sample holders 146 for holding the assay sample. Further included in the immunological system 100 may optionally be tubes with the assay sample 147 and/or tubes with reagent 148.

In one embodiment, the vessel 105 is a filter vessel. "Filter vessel" 105 means a vessel capable of containing an assay sample and including one or more filters 150 disposed therein. Preferably, the filter vessel 105 includes a filter 150 including an inert material and a plurality of pores. In the preferred embodiment, a plurality of filter vessels 105 are arranged into a single unit, such as a plate 106. Hereinafter, vessel 105 may be referred to as filter vessel 105, but in other embodiments, vessel 105 may be another type of vessel, such as a vessel with a bottom surface having an uneven topography, as discussed above.

The optional incubator 110 disposed within the immunological system 100 is of a shape and size that allows filter vessel 105 to be disposed therein. While many sizes and shapes of an incubator may be used, in a preferred embodiment, the incubator 110 is of a shape and size so as to allow a plurality of filter vessels 105 or a plate of filter vessels 106 to be disposed therein. The incubator 110 may further include an optional heating element capable of heating the filter vessels 105 when they are disposed in the incubator 110.

The sample separation system 115 is also of a shape and size so as to allow a filter vessel 105 to be disposed therein. While many sizes and shapes of a sample separation system may be used, in the preferred embodiment, a plurality of filter vessels 105 and/or a plate of filter vessels 106 may be disposed therein. The sample separation system 115 may be, for example, but is not limited to, a centrifuge 125, a filtration system, and/or an applied electric field. The sample separation system 115 is of a type that when the filter vessel 105 is placed within the sample separation system 115, an assay sample 147 disposed within the filter vessel 105 is drawn through a filter 150, thereby separating out the assay sample into various components based on size. In an alternative embodiment, where the sample separation system 115 may be a centrifuge 125, the process of centrifugation will cause any reacted components, such as RBCs, in the assay sample 147 to spread out evenly over the bottom surface of the vessel such that they can be washed with the optional washer 140 and analyzed with the image acquisition system 130 without RBC agglutination.

The optional image acquisition system 130 may be, for example, but is not limited to, a camera, a flow cytometer, a capillary cytometer, a special lens such as a microscope, or even a human eye. Usually, an assay sample is analyzed by the image acquisition system 130 after it has been removed from the sample separation system 115. The image acquisition system 130 may also allow analysis of the filter vessel 105 in order to determine the presence or absence of material above the filter 150 disposed within the vessel.

The image acquisition system 130, particularly when it takes the form of a flow cytometer or a capillary cytometer, may also be used to determine the size and reacted state of the material above the filter 150. For example, the image acquisition system 130 may determine whether the material is in the form of individual antigen carriers or aggregates of antigen carriers, as well as determine whether or not fluorescently-labeled antibodies are bound to the antigen carriers that are present above the filter 150, or in the vessel if no filter 150 is present.

The optional robotic pipettor 135 used within the system is of the type commonly known and used by those skilled in the art. For example, but not limited to, the robotic pipettor system that is manufactured by and commercially available from Tomtec, Inc. (Hamden, Conn., U.S.A.) or CRS Robotics Corporation (Burlington, Ontario, Canada) may be used in accordance with one embodiment.

The optional washer 140 is disposed within reaching distance of a robotic arm of the robotic pipettor 135 from the image acquisition system 130. The washer 140 is of a size and shape so as to allow the filter vessel 105, a plurality of filter vessels 105, and/or a plate of filter vessels 106 to be disposed therein. The washer 140 is designed so as to wash all reagents from the antigen carriers present in the assay mixture, and through the filter 150 of the filter vessel 105. Alternatively, when antigen carriers such as RBCs are evenly dispersed over the bottom of the filter vessel 105 following centrifugation, the washer 140 may be used to aspirate or pipette off the fluid overlying the RBC layer, and then subsequently pipette or otherwise dispense more fluid onto the RBCs. These steps that comprise washing may be repeated multiple times. While there may be many configurations of the washer 140, the washer 140 may be a vacuum or a pipetting system.

Figure 2:
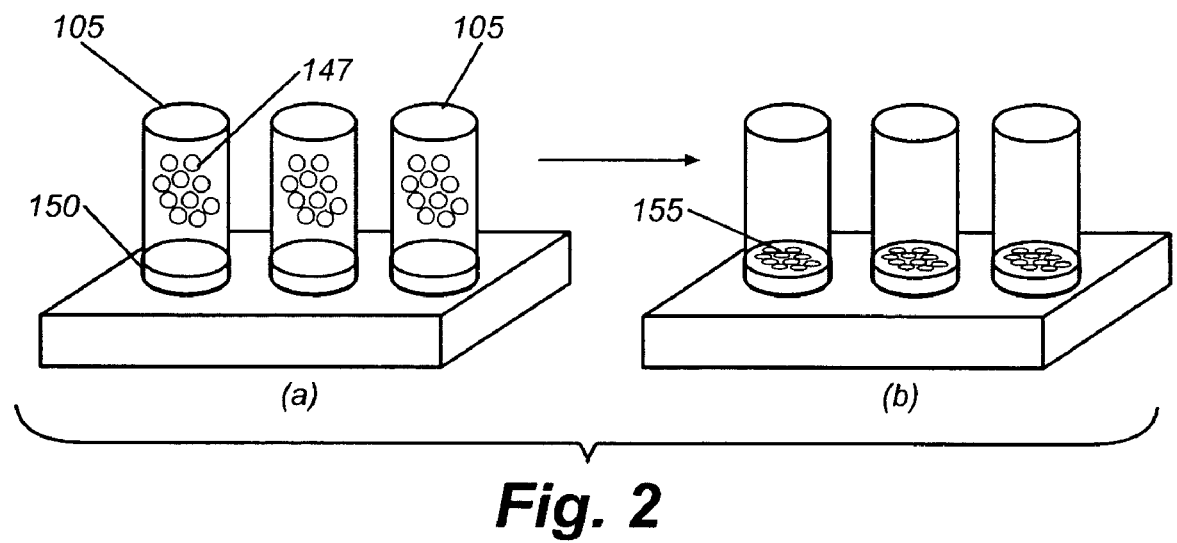
FIGS. 2(a) and (b) illustrate interactions between a sample and reagent mixture in a filter vessel of the immunological system of FIG. 1.

FIG. 2 depicts one exemplary filter vessel 105 component of the immunological system 100 of FIG. 1. FIG. 2 represent a plurality of filter vessels 105 (a) in a plate configuration 106 containing a sample 147 to be analyzed, before being placed in a centrifuge 125 for sample separation, and (b) after removal from the centrifuge 125. As seen in FIG. 2, disposed within the filter vessel 105 is a filter 150. Note that following centrifugation the antigen carriers 155 are evenly dispersed over the bottom of the filter 150 in the filter vessels 105.

The pore size of the filter 150 may be varied, according to the various embodiments. For example, pores of the filter 150 may be of a size ranging from approximately 0.01 microns ($\mu$m) to approximately 50 $\mu$m. The size of the pores of the filter 150 will depend on the application of the filter vessel 105. If it is desired that the filter 150 be used to retain, for example, RBC aggregates, while allowing individual red blood cells to pass through the pores of the filter 150, in one embodiment of this application, the range of pore sizes is between approximately 3 $\mu$m to approximately 40 $\mu$m. If, however, the filter vessel 105 is used to filter only fluid away from the antigen carriers (e.g., RBCs, WBCs, platelets, or synthetic beads) where the filter 150 is used to retain the antigen carriers, but allow fluid containing antibodies to pass therethrough, the range of pore sizes in the preferred embodiment is approximately 0.1 $\mu$m to approximately 3 $\mu$m. More preferably, the pore size ranges from approximately 0.2 $\mu$m to approximately 1.2 $\mu$m. The optimal pore size for this methodology is 0.45 $\mu$m.

When the filter 150 contains very small pore size, e.g., from approximately 0.2 $\mu$m to approximately 1.2 $\mu$m, the filter may not even effectively filter the fluid away from the antigen carriers. In this case, the filter 150 can act as an uneven surface of irregular topography which causes the reacted components in the assay sample to spread out evenly over the bottom surface of the filter vessel when the filter vessels 105 are placed into the sample separation system 115, for example a centrifuge 125. The even spreading of the RBCs or other antigen carriers over the bottom of the filter vessel following centrifugation reduces aggregation or agglutination of the antigen carriers and makes it easier and more accurate for the image acquisition system 130 to analyze the presence of interactions in the assay sample, particularly if the image acquisition system 130 is a flow cytometer or a capillary cytometer.

The thickness of the filter 150 may also vary in the different embodiments of the filter vessel 105, depending upon the application of the filter 150. For example, the thickness of the filter 150 may range from approximately 3 $\mu$m to approximately 5 mm. In the preferred embodiment the filter 150 is between approximately 3 $\mu$m to approximately 100 $\mu$m. Optimally, the thickness of the filter 150 is between approximately 10 $\mu$m and approximately 75 $\mu$m.

As noted above, in the various embodiments of the filter vessel 105, the filters 150 may be made from many different types of material. In the preferred embodiment, the filter 150 includes an inert material and a plurality of pores. The inert material of the filter 150 may be varied, depending on the application of the filter 150.

If, for example, the function of the filter 150 is to cause the reacted components to spread out evenly over the surface of the filter 150 after centrifugation, the inert material of the filter 150 may be for example, but not limited to, a polypropylene, a nylon, a cellulose nitrate and a polyvinylidene fluoride material. Preferably, the filter 150 is made of one of the following: polypropylene with 0.45 $\mu$m-sized pores (manufactured by and commercially available as UniFilter® from Whatman plc of Kent, U.K.); cellulose nitrate with 0.45 $\mu$m-sized pores (manufactured by and commercially available as UniFilter® from Whatman plc); nylon 6,6 with 0.45 $\mu$m-sized pores (manufactured by and commercially available as Silent Screen™ from Nalge Nunc International of Rochester, N.Y., USA); nylon 6,6 with 1.2 $\mu$m-sized pores (manufactured by and commercially available as Silent Screen™ from Nalge Nunc International); HPVM membrane with 0.2 $\mu$m-sized pores (manufactured by and commercially available from Nalge Nunc International of Rochester, N.Y., USA); polyvinylidene fluoride (PVDF) with 1.0 $\mu$m-sized pores (manufactured by and commercially available as MultiScreen® from Millipore Inc. of Bedford, Mass., USA); PVDF with 1.2 $\mu$m-sized pores (manufactured by and commercially available from Millipore Inc.); PVDF with 0.2 $\mu$m-sized pores (manufactured by and commercially available from Coming Life Sciences of Acton, Mass., USA); and PVDF with 0.25 $\mu$m-sized pores (manufactured by and commercially available from Coming Life Sciences). It has been found that the polypropylene with 0.45 $\mu$m-sized pores works as the optimum filter material 150 in one embodiment.

Figure 3:
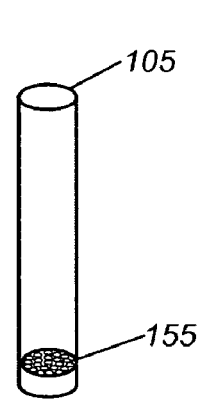
FIG. 3 is a diagram illustrating a representative filter vessel of the immunological system of FIG. 1, depicting interacted sample and reagents.

FIG. 3 illustrates an alternate embodiment vessel 106 to the vessel 105 depicted in FIG. 2. The vessel 106 may be substituted for the vessel 105 in the immunological system 100. The vessel 106 may includes a bottom with the uneven topography discussed above, or any of the filter materials discussed above. The uneven topography or filter material aids in evenly spreading the antigen carriers 155 over the bottom surface of the vessel 106 following centrifugation as discussed below.

Figure 4:
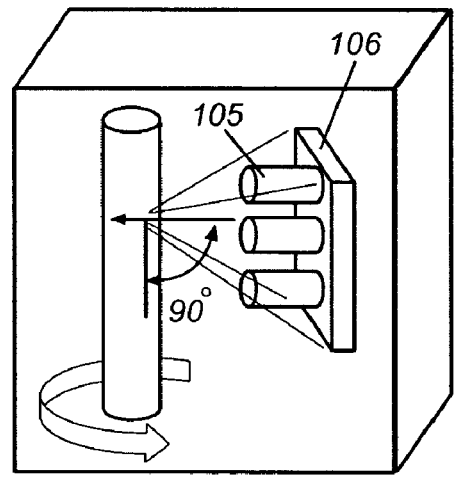
FIG. 4 is a diagram illustrating a representative separation system component of the immunological system of FIG. 1, as an exemplary centrifuge in operation.

FIG. 4 depicts the centrifuge 125, which is one type of the sample separation system 115, a component of the immunological system 100. It should be understood that any type of centrifuge system known and used by those skilled in the art may be used as the centrifuge 125. For example, a typical centrifuge manufactured by and commercially available from Beckman Coulter, Inc (Fullerton, Calif., U.S.A.) may be used in accordance with one embodiment, so long as the centrifuge is modified to hold the filter vessels 105 and/or a filter plate 106. The centrifuge 125 shown in FIG. 4 shows the angle of centrifugation used in the preferred embodiment. While many angles could work, in a preferred embodiment the filter vessel 105 is placed in a "swinging bucket rotor," which begins at an angle of 0° relative to the axis of rotation 175 when the centrifuge is at rest, moves to an angle of 90° during centrifugation, and returns to an angle of 0° at the end of centrifugation.

In one embodiment of the immunological system 100, the orientation of the filter vessel 105, the sample, and the filter 150 is such that the sample separation system 115 can cause the sample to contact the filter 150 and allow components of the sample that are smaller than the nominal pore size of the filter 150 to pass through the filter 150 into a capture reservoir below the filter 150, and thus be separated from the components of the sample that are too large to fit through the filter pores and that remain in the filter vessel 105 above the filter 150.

In one embodiment of the immunological system 100, the vessel 105 may include a bottom with the uneven topography discussed above, or any of the filter materials discussed above. The uneven topography or filter material aids in spreading the antigen carriers 155 evenly over the bottom surface of the vessel 105. The uneven topography, or the filter material prevents the antigen carriers 155 from migrating to only one portion or side of the vessel 105 during centrifugation. If the antigen carriers 155 migrate to one portion of the vessel 105 during centrifugation, then antigen carriers 155 may become agglutinated into large clumps and be difficult to disperse and accurately read via the image acquisition system 130. Thus, the vessel 105 improves the results able to be obtained from the image acquisition system 130, particularly when image acquisition system 130 is a flow cytometer or a capillary cytometer.

Another embodiment includes an immunological assay method. Generally, the method includes mixing a diluted immunohematological sample with a diluted reagent to form a sample mixture, analyzing the sample mixture via flow cytometry, and determining whether a predetermined component is present in the immunohematological sample. The method may be applied, for example, the following types of assays.

ABO/D Forward Typing

One embodiment of the disclosed method uses a primary mouse antibody unlabeled, and then detects its presence using a commercially available fluorescently labeled secondary antibody directed against mouse immunoglobulin M (IgM).

In order to render this technology applicable to blood typing using flow cytometry, the following methods may be employed. The primary IgM antibody is diluted to the point where RBC agglutination does not occur, or occurs to only a minimal extent, following mixing of RBCs and antibodies, and subsequent washing of RBCs. While many potential dilutions can be used, an approximate 1:500 to 1:1000 dilution provides optimal results. This method reduces reagent costs associated with forward-typing. Until this disclosed method, it has generally been believed in the field that high antibody titers are necessary for sensitive blood typing. With the present method, however, substantial experimental data shows that sensitive blood typing can be performed using the above antibody dilutions because of the sensitive detection available by flow cytometry. For example, representative data is shown in Table 1, where different dilutions of anti-A antibody (1:50 to 1:1000) were used to stain either Group O RBCs (which do not have A antigen) or Group A RBCs (which do have A antigen). The fluorescent signal of the RBCs was acquired by flow cytometry, and the mean fluorescence was calculated. Note that Group O RBCs have extremely low fluorescence since they do not have A antigen. It is notable that even when the anti-A antibody is diluted to 1:1000, the mean fluorescence of Group A RBCs (19.5) is still significantly greater than that of Group O RBCs (4.11). Thus, the antibodies commonly used for immunohematology testing can be diluted to much lower concentrations than is generally believed to be possible in the field when antibody-RBC interactions are detected by flow cytometry.

TABLE 1

Representative Data Demonstrating Sensitivity of Flow Cytometry for Detecting Antibody-Antigen Interactions, Even at Low Antibody Concentrations

| | Mean Fluorescence Intensity of RBCs | |
|---|---|---|
| Antibody dilution | Group O RBC | Group A RBC |
| Anti-A (1:50) | 4.18 | 179.82 |
| Anti-A (1:100) | 4.19 | 79.75 |
| Anti-A (1:500) | 4.11 | 36.4 |
| Anti-A (1:1000) | 4.11 | 19.5 |

The secondary antibody is desirably also used at an appropriate dilution. Use of antibodies with titers that are too high will usually produce agglutination. While many potential dilutions can be used, an approximate 1:100 dilution provides optimal results. Again, this method also reduces reagent costs associated with forward-typing. Although IgM molecules are usually difficult to directly conjugate with fluorescent tags, the preparation of labeled IgM antibodies would obviate the need to use secondary antibodies, and would thus decrease agglutination. Furthermore, in standard uses of flow cytometry to detect antigens on cells, most antibodies must be incubated with the cells at 4° C. Thus, unexpectedly, the secondary antibody incubations can be effectively performed at an approximate 1:100 dilution at room temperature.

Finally, even using appropriate antibody dilutions as above, some agglutination may nevertheless occur if cells are washed by centrifuging in a typical tube because all the cells are brought together into a tight single pellet that can be cross-linked by the antibodies. This level of agglutination may be too great for flow cytometric analysis. Thus, in addition to the use of appropriate dilutions of primary and secondary antibodies, as described above, washing procedures may be employed that do not allow strong RBC agglutination. Two such procedures are known: (1) the Rapid Automated Flow cytometric Testing (RAFT) technology, which employs vacuum filtration, spreads cells out on the filter so they are not close enough to one another to be effectively crosslinked. This technology was described in U.S. provisional patent application 60/179,248, U.S. patent application Ser. No. 09/773,826, and Patent Cooperation Treaty patent application PCT/US01/03206, all of which are incorporated herein by reference; and (2) rather than using vacuum filtration, the microtiter filter plates are centrifuged at low speed, as described herein below.

As mentioned above, conventional assay methods have traditionally required that three separate tubes/reactions be set up to detect the presence of A, B, and Rh(D) antigens on RBCs. By using flow cytometry in the disclosed methods and devices, however, all three antigens to be detected simultaneously in a single tube. This type of multiplexing can be performed in a number of ways.

In one embodiment, anti-A, anti-B, and anti-Rh(D) antibodies can each be separately directly labeled with a different fluorescent reporter molecule. For example, human IgG anti-Rh(D) antibodies may be used for this application by directly labeling them with fluorescein isothiocyanate (FITC) using commercially available kits. In an alternative embodiment, if IgM antibodies are derived from different species (e.g., human IgM anti-A and mouse IgM anti-B), then different secondary antibodies (containing different fluorescent tags) can be used that would distinguish between them (e.g., goat anti-human IgM and goat anti-mouse IgM).

ABO Back Typing

In contrast to forward typing, it is not possible to control the strength of the primary antibody since it will vary from patient to patient. For this reason, the use of appropriate methodology during washing prevents RBC agglutination. As above, this method uses either the technology described in U.S. patent application Ser. No. 09/773,826, and international patent application PCT/US01/03206, or that described herein below. As with forward typing, the titer of the secondary antibody is appropriately determined in order to limit agglutination. The details are shown in Table 2 below of an example of such a method of ABO back typing of blood.

sample in the filter vessel 105 or vessel 106. As shown in block 190, the next step includes adding assay reagents to the filter vessel 105 or 106. The next optional step, shown in block 195, is mixing the sample with the reagent to form a sample mixture 200. As shown in block 205, the method includes an optional step of incubating the sample mixture 200.

In the incubation step, as shown in block 205, the sample mixture 200 may be incubated at a temperature ranging from approximately 4° C. to approximately 37° C. In a preferred embodiment, the sample mixture 200 is incubated at a temperature range between approximately room temperature (20-25° C.) and approximately 37° C. The incubation time of the sample mixture 200 can range from no incubation to approximately a 30-minute incubation time. In a preferred embodiment, the incubation time ranges from approximately 2 to approximately 5 minutes.

After the optional incubation, the next optional step, as depicted in block 210, is to separate the sample mixture 200 into its various components. This step is usually accomplished by placing the filter vessel 105 and/or plate 106 containing the sample mixture 200 in the sample separation system 115. If the sample separation system 115 used in the separating step of block 210 is the centrifuge 125, the centrifuge speed is preferably at a rate from approximately 100 to approximately 1,000× acceleration of gravity (g), although other speeds may be used. In the preferred embodiment, the maximum speed of the centrifuge ranges from approximately 250 g to 400 g. The centrifuge time may range from approximately 5 seconds to approximately 5 minutes. Although other times may be used, in the preferred embodiment, the maximum centrifuge time is approximately 1 minute.

After the sample is centrifuged the RBCs or other antigen carriers are dispersed evenly on the bottom of the vessel, and the overlying fluid may contain residual antibodies or other reagents that have not reacted with the antigen carriers. The

TABLE 2

Example Flow Cytometry ABO/Rh(D) Testing Protocols

| | ASSAY | | | |
|---|---|---|---|---|
| Step | A, B Forward | Rh (D) Forward | A, B Reverse | Antibody Screen |
| 1. RBC | 2% patient RBC 25 µl | 2% patient RBC 25 µl | 3% A, B, O RBC 30 µl | 3% screening cells 13 µl |
| 2. Primary Ab | Mse α-A, α-B 50 µl | Human α-Rh(D) 50 µl | Patient plasma 50 µl | Patient plasma 25 µl |
| 3. Potentiator | — | — | — | PEG (20%) 50 µl |
| 4. Incubation | RT × 2 min | RT × 2 min | RT × 2 min | 37° C. × 5 min |
| 5. Wash | 200 µl saline × 4 | 200 µl saline × 4 | 200 µl saline × 4 | 200 µl saline × 4 |
| 6. Secondary Ab | PE-α-mse IgM 100 µl | PE-α-hum IgM 100 µl | PE-α-hum IgM 100 µl | PE-α-hum IgG 100 µl |
| 7. Incubation | RT × 5 min | RT × 5 min | RT × 5 min | RT × 5 min |
| 8. Wash | 200 µl saline × 2 | 200 µl saline × 2 | 200 µl saline × 2 | 200 µl saline × 2 |
| 9. | | Flow cytometry | | |

Screening for Unexpected RBC Alloantibodies

The disclosed assay method for screening for unexpected RBC alloantibodies is similar to that described above for back typing. For example, the disclosed assay can be performed according the example in Table 2 above.

Figure 5:
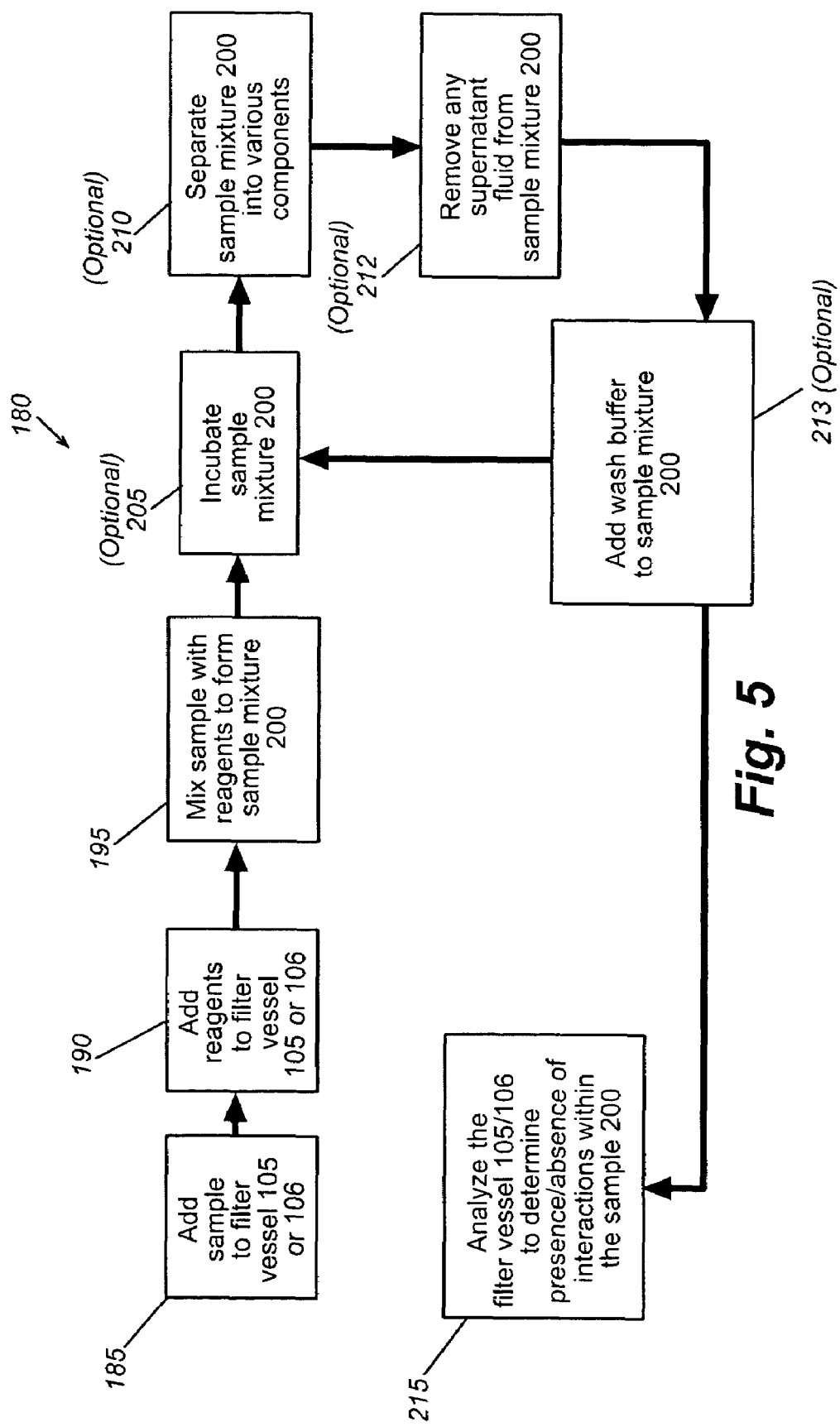
FIG. 5 is a flowchart of a representative disclosed immunological assay method, which uses the immunological system of FIG. 1.

Yet another embodiment includes an immunological assay method 180 as depicted in the flowchart of FIG. 5. The immunological assay method 180 includes the optional step of, as can be seen in block 185, placing an immunologicalassay supernatant fluid may optionally be removed from the vessel 105/106, as shown in block 212. Removal may be accomplished for example, but not limited to, by pipetting, such as robotic pipetting, or simply pouring off the non-reacted components.

If supernatant fluid is removed, the antigen carriers remaining on the bottom of the filter vessel may optionally be washed. This washing procedure can be accomplished by adding a buffer solution to the antigen carriers, as shown in block 213. The buffer solutions may be for example, but not limited to, saline, e.g., 0.9% sodium chloride (NaCl) solution; a phosphate-buffered saline; or any physiological salt solution that preserves the viability of cellular components during the assay method. In the preferred embodiment a solution of 0.9% (w/v) NaCl, pH 7.4 is used. The buffer may be added by pipetters or other means.

After adding buffer solution, the buffer may optionally be incubated with the antigen carriers as shown in block 205, optionally followed by separating the antigen carriers from the supernatant fluid as in block 210, and optionally removing the supernatant fluid as in block 212. This process may be repeated from one to approximately ten times, until the sample mixture 200 is washed sufficiently for the application.

The washing step may include the steps of providing the physiological salt solution, and adding approximately 10 microliters to approximately 5 milliliters of the physiological salt solution to the sample mixture 200. Following the optional washing steps encompassed in blocks 205, 210, 212, and 213, the sample may be reacted with additional reagents, such as other antibodies, by proceeding to the step shown in block 190. The steps may be repeated in the order illustrated by the arrows any chosen number of times, but preferably between one and five.

As shown in block 215, after the optional separation step 210, the optional fluid removal step 212, and the optional washing step 213, the filter vessel 105 and/or plate 106 may optionally be analyzed to determine the presence or absence of interactions within the sample 200. The sample 200 is analyzed by placing the filter vessel 105 and/or plate 106 in the image acquisition system 130. If interactions between assay sample and reagent are detected in the material above the filter 150 by the acquisition system 130 in the analyzing step, as shown in block 215, the immunological assay method 180 is completed. Assay results will be determined based on whether there have been interactions, for example, between cellular components in the assay sample and antibody reagents.

The interaction may evidence itself in the form of agglutination, or clumping together, of the cellular components by the antibodies. This agglutination may be detected by the image acquisition system 130. Similarly, the assay method may be used to detect interactions between antibody components in the assay sample and cellular reagents by detecting presence or absence of agglutination of cellular reagents by the antibody components by the image acquisition system 130. Alternatively, the antibodies used in these assays may be conjugated to fluorescent dyes or otherwise labeled. In this case, interactions between labeled antibodies and antigen carriers can be detected with a flow cytometer or a capillary cytometer as fluorescent labeling of the antigen carrier. In this embodiment, it is preferable that any agglutination of the RBCs or other antigen carriers be minimized.

It should be emphasized that the above-described embodiments of the disclosed assay systems and methods, are merely possible examples of implementations, and are merely set forth for a clear understanding of the principles disclosed herein. Many variations and modifications may be made to the above-described embodiment(s) without departing substantially from the spirit and principles of the invention. All such modifications and variations are intended to be included herein within the scope of this disclosure and protected by the following claims.

Now, therefore, the following is claimed:

1. An immunological assay system, comprising:
    a vessel capable of containing an assay sample and a reagent,
    wherein the vessel comprises a bottom with an uneven surface, wherein the bottom of the vessel comprises a filter material chosen from at least one of the following: polypropylene with 0.45 micron (μm)-sized pores; cellulose nitrate with 0.45 μm-sized pores; nylon 6,6 with 0.45 μm-sized pores; nylon 6,6 with 1.2 μm-sized pores; HPVM membrane with 0.2 μm-sized pores; polyvinylidene fluoride (PVDF) with 1.0 μm-sized pores; PVDF with 1.2 μm-sized pores; PVDF with 0.2 μm-sized pores; and PVDF with 0.25 μm-sized pores, wherein the filter material provides the uneven bottom surface and is configured to cause reacted components to spread out over the uneven bottom surface while substantially preventing reacted components from passing through the filter material;
    an image acquisition system in close proximity to the vessel,
    wherein the image acquisition system is designed to detect the presence of interactions between components in the assay sample and the reagent, wherein said interactions are evidenced by agglutination,
    wherein the image acquisition system consists of a flow cytometer or a capillary cytometer, and wherein the image acquisition system in close proximity to a sample separation system; and
    an incubator in which the vessel may be placed, wherein the incubator houses the vessel while the assay sample and the reagents react.

2. The immunological assay system of claim 1, further comprising a sample separation system in close proximity to the incubator, wherein the sample separation system is designed to separate the assay sample and the reagents into various components.

3. The immunological assay system of claim 1, further comprising a robotic pipettor including a robotic arm within reaching distance of the vessel, the incubator, the sample separation system and the image acquisition system, wherein the robotic pipettor is designed to transfer the assay sample or the reagents between the vessel, incubator, the sample separation system and the image acquisition system.

4. The system of claim 2, wherein the sample separation system is a centrifuge.

5. The system of claim 1, wherein the assay sample comprises red blood cells and antibodies.

6. The system of claim 1, further comprising means for spreading the reacted sample and reagent components evenly over the bottom surface of the vessel.

7. The system of claim 6, wherein the means for spreading the reacted sample and reagent components evenly over the bottom surface of the vessel is a centrifuge.

8. The system of claim 1, further comprising means for analyzing the reacted components on the bottom surface of the vessel.

9. An immunological assay system, comprising:
    a reaction vessel comprising a bottom with an uneven surface, wherein the bottom of the vessel comprises a filter material chosen from at least one of the following: polypropylene with 0.45 micron (μm)-sized pores; cellulose nitrate with 0.45 μm-sized pores; nylon 6,6 with 0.45 μm-sized pores; nylon 6,6 with 1.2 μm-sized pores; HPVM membrane with 0.2 μm-sized pores; polyvinylidene fluoride (PVDF) with 1.0 μm-sized pores; PVDF with 1.2 μm-sized pores; PVDF with 0.2 μm-sized pores; and PVDF with 0.25 μm-sized pores, wherein the filter material provides the uneven bottom surface and is configured to cause reacted components to spread out over the uneven bottom surface while substantially preventing reacted components from passing through the filter material;

an incubator in which the vessel can be placed, wherein the incubator houses the vessel while the assay sample and the reagents react;

a dilute concentration of an immunohematological sample;

a dilute concentration of a reagent;

an image acquisition apparatus, wherein the image acquisition apparatus consists of a flow cytometer or a capillary cytometer, wherein the cytometer is designed to detect the presence of interactions between components in the assay sample and the reagent, wherein the interactions are evidenced by agglutination; and a centrifugation system configured of a shape and size so as to allow the reaction vessel to be disposed therein.

10. The system of claim 9, wherein the immunohematological sample comprises at least one of red blood cells, antigens, and alloantibodies.

11. The system of claim 9, wherein the reagent comprises at least one of an antibody and patient plasma.

12. The system of claim 9, wherein the system detects at least one of A-antigen, B-antigen, Rh(D)-antigen, Kell antigen, Duffy antigen, antibody, and alloantibody.

13. The system of claim 9, wherein the system detects at least two of A-antigen, B-antigen, Rh(D)-antigen, Kell antigen, Duffy antigen, antibody, and alloantibody.

14. The system of claim 9, wherein the system detects at least three of A-antigen, B-antigen, Rh(D)-antigen, Kell antigen, Duffy antigen, antibody, and alloantibody.

15. An immunological assay method comprising:

providing a vessel having a bottom with an uneven surface, wherein the bottom of the vessel comprises a filter material chosen from at least one of the following: polypropylene, cellulose nitrate, nylon, polyvinylidene fluoride, and HPVM membrane, the filter material including a plurality of pores with a pore size from about 0.2 microns to about 1.2 microns, wherein the filter material provides the uneven surface and substantially prevents interacted components from passing through the filter material;

reacting an immunological sample and a reagent mixture in the vessel;

centrifuging the sample and reagent mixture in the vessel, wherein the uneven surface causes the interacted components in the sample to spread evenly over the bottom surface of the vessel during centrifugation, without migrating to a single area within the vessel; and analyzing the reacted components on the bottom surface in the vessel to determine the presence of interactions between the sample and reagent components, wherein the interactions are evidenced by agglutination, and wherein the interactions are analyzed via a flow cytometer or a capillary cytometer.

16. The method of claim 15, wherein the centrifugation is at low speed.

17. The method of claim 16, wherein the centrifugation at low speed comprises centrifugation at a maximum rate of approximately 1,000 g.

18. The method of claim 16, wherein the centrifugation at low speed comprises centrifugation at a rate from approximately 250 g to approximately 400 g.

19. The method of claim 15, further comprising separating from the vessel any portion of the sample and reagent mixture that did not react.

20. The method of claim 15, further comprising incubating the sample and reagent mixture.

21. The method of claim 15, wherein the sample and reagent mixture comprises red blood cells and antibodies.

22. The method of claim 15, wherein the vessel comprises a filter including an inert material, and a plurality of pores.

23. The method of claim 22, wherein the filter comprises a material selected from the group consisting of: polypropylene with 0.45 micron (μm)-sized pores; cellulose nitrate with 0.45 μm-sized pores; nylon 6,6 with 0.45 μm-sized pores; nylon 6,6 with 1.2 μm-sized pores; HPVM membrane with 0.2 μm-sized pores; polyvinylidene fluoride (PVDF) with 1.0 μm-sized pores; PVDF with 1.2 μm-sized pores; PVDF with 0.2 μm-sized pores; and PVDF with 0.25 μm-sized pores.

24. The method of claim 15, wherein the centrifugation is for a short period of time.

25. The method of claim 15, wherein the centrifugation is for a maximum time of approximately 1 minute.

26. The method of claim 15, wherein reacting the sample and reagent mixture comprises incubating the sample and reagent mixture.

27. The method of claim 15, wherein the centrifugation is at low speed and for a short period of time.

28. An immunological assay method, comprising:

mixing a diluted immunohematological sample with a diluted reagent to form a sample mixture in a vessel with an uneven bottom surface, wherein the uneven bottom surface of the vessel comprises a filter material having a bottom surface immediately adjacent a bottom of the vessel and an uneven top surface, wherein the filter material is chosen from at least one of the following: polypropylene with 0.45 micron (μm)-sized pores; cellulose nitrate with 0.45 μm-sized pores; nylon 6,6 with 0.45 μm-sized pores; nylon 6,6 with 1.2 μm-sized pores; HPVM membrane with 0.2 μm-sized pores; polyvinylidene fluoride (PVDF) with 1.0 μm-sized pores; PVDF with 1.2 μm-sized pores; PVDF with 0.2 μm-sized pores; and PVDF with 0.25 μm-sized pores;

analyzing the sample mixture via flow cytometry; and determining whether a predetermined component is present in the immunohematological sample by determining the presence of agglutination with the flow cytometry; and spreading the sample mixture over the top surface of the filter material through low speed centrifugation in order to facilitate interactions between reaction components, while substantially preventing reacted components from passing through the filter material.

29. The method of claim 28, wherein the immunohematological sample comprises at least one of red blood cells, antigens, and alloantibodies.

30. The method of claim 28, wherein the reagent comprises at least one of an antibody and patient plasma.

31. The method of claim 28, wherein the predetermined component is at least one of A-antigen, B-antigen, Rh(D)-antigen, Kell antigen, Duffy antigen, antibody, and alloantibody.

32. The method of claim 28, wherein the predetermined component is at least two of A-antigen, B-antigen, Rh(D)-antigen, Kell antigen, Duffy antigen, antibody, and alloantibody.

33. The method of claim 28, wherein the predetermined component is at least three of A-antigen, B-antigen, Rh(D)-antigen, Kell antigen, Duffy antigen, antibody, and alloantibody.

34. The method of claim 28, further comprising:

spreading the sample mixture over a bottom surface of a reaction vessel through vacuum filtration.

35. An immunological assay system, comprising:
a vessel capable of containing an assay sample and a reagent,
wherein the vessel comprises a bottom with an uneven surface, wherein the uneven surface comprises a filter material immediately adjacent to the bottom of the vessel configured to substantially prevent reacted components from passing through the filter material and to cause reacted components in the assay sample to spread out on top of uneven surface of the filter material, wherein the filter material is chosen from at least one of the following: polypropylene with 0.45 micron (μm)-sized pores; cellulose nitrate with 0.45 μm-sized pores; nylon 6,6 with 0.45 μm-sized pores; nylon 6,6 with 1.2 μm-sized pores; HPVM membrane with 0.2 μm-sized pores; polyvinylidene fluoride (PVDF) with 1.0 μm-sized pores; PVDF with 1.2 μm-sized pores; PVDF with 0.2 μm-sized pores; and PVDF with 0.25 μm-sized pores;
an image acquisition system in close proximity to the vessel,
wherein the image acquisition system is designed to detect the presence of interactions between components in the assay sample and the reagent, wherein said interactions are evidenced by agglutination,
wherein the image acquisition system consists of a flow cytometer or a capillary cytometer, and wherein the image acquisition system in close proximity to a sample separation system; and
an incubator in which the vessel may be placed, wherein the incubator houses the vessel while the assay sample and the reagents react.

36. An immunological assay system, comprising:
a vessel capable of containing an assay sample and a reagent,
wherein the vessel comprises a bottom with an uneven surface, wherein the uneven surface comprises a single piece of a filter material having a bottom surface immediately adjacent to the bottom of the vessel and a top surface configured to cause reacted components in the assay sample to spread out over the top surface of the filter material, wherein the filter material is chosen from at least one of the following: polypropylene, cellulose nitrate, nylon, polyvinylidene fluoride, and HPVM membrane, the filter material including a plurality of pores with a pore size from about 0.2 microns to about 1.2 microns;
an image acquisition system in close proximity to the vessel,
wherein the image acquisition system is designed to detect the presence of interactions between components in the assay sample and the reagent, wherein said interactions are evidenced by agglutination, and wherein the image acquisition system consists of a flow cytometer or a capillary cytometer.

* * * * *